United States Patent
Garcia-Cardena et al.

(10) Patent No.: US 9,006,149 B2
(45) Date of Patent: Apr. 14, 2015

(54) HIGH-THROUGHPUT BIOLOGICAL SCREENING

(75) Inventors: Guillermo Garcia-Cardena, Cambridge, MA (US); Peter Mack, Chapel Hill, NC (US); Jeffrey T. Borenstein, Newton, MA (US); Ahmad S. Khalil, Brookline, MA (US); Eli J. Weinberg, Needham, MA (US); Jason O. Fiering, Boston, MA (US); Ernest S. Kim, Cambridge, MA (US); William J. Adams, Jr., Cambridge, MA (US)

(73) Assignees: The Charles Stark Draper Laboratory, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 12/687,717

(22) Filed: Jan. 14, 2010

(65) Prior Publication Data
US 2010/0323916 A1 Dec. 23, 2010

Related U.S. Application Data

(60) Provisional application No. 61/145,037, filed on Jan. 15, 2009.

(51) Int. Cl.
C40B 30/06 (2006.01)
C40B 60/12 (2006.01)
C12M 1/32 (2006.01)
C12M 1/42 (2006.01)

(52) U.S. Cl.
CPC ............. *C12M 23/12* (2013.01); *C12M 35/04* (2013.01)

(58) Field of Classification Search
CPC .................................................... C12M 35/04
USPC ........................................................... 506/10
See application file for complete search history.

(56) References Cited

U.S. PATENT DOCUMENTS

| 1,502,865 | A | | 7/1924 | Moody |
| 3,575,525 | A | | 4/1971 | Fox et al. |
| 4,507,048 | A | | 3/1985 | Belenger et al. |
| 4,652,207 | A | | 3/1987 | Brown et al. |
| 4,984,972 | A | | 1/1991 | Clausen et al. |
| 5,055,263 | A | * | 10/1991 | Meltzer ......................... 422/65 |

(Continued)

OTHER PUBLICATIONS

Blackman et al. "A New In Vitro Model to Evaluate Differential Responses of Endothelial Cells Simulated Arterial Shear Stress Waveforms," Journal of Biomechanical Engineering, vol. 124, Aug. 2002, pp. 397-407.

(Continued)

*Primary Examiner* — Larry Riggs
*Assistant Examiner* — Karla Dines
(74) *Attorney, Agent, or Firm* — Edward A. Gordon; Foley & Lardner LLP

(57) ABSTRACT

A high-throughput flow system includes an array of wells and a separate mechanical tip positioned within each well. Each mechanical tip is separately actuated to impart a shear stress pattern. A separate sleeve may be associated with each tip for maintaining a predetermined distance between the tip and a floor of the tip's corresponding well, with each tip being rotatable within its corresponding sleeve. Alternatively, a separate post may be associated with each tip for maintaining a predetermined distance between the tip and a floor of the tip's corresponding well, with each tip being rotatable about its corresponding post.

46 Claims, 12 Drawing Sheets

(56) References Cited

U.S. PATENT DOCUMENTS

| | | | |
|---|---|---|---|
| 5,399,074 A | 3/1995 | Nose et al. | |
| 5,803,720 A | 9/1998 | Ohara et al. | |
| 6,116,099 A * | 9/2000 | Carl | 73/864.14 |
| 6,206,659 B1 | 3/2001 | Izraelev | |
| 6,547,539 B2 | 4/2003 | Izraelev | |
| 6,655,194 B2 * | 12/2003 | Hajduk et al. | 73/54.37 |
| 6,769,292 B2 * | 8/2004 | Mansky et al. | 73/54.32 |
| 7,063,942 B2 | 6/2006 | Dancu et al. | |
| 7,476,077 B2 | 1/2009 | Woodard et al. | |
| 7,482,169 B2 * | 1/2009 | Gjerde et al. | 436/178 |
| 8,460,622 B2 * | 6/2013 | Motadel | 422/564 |
| 2003/0124007 A1 | 7/2003 | Schima et al. | |
| 2004/0123650 A1 * | 7/2004 | Kolosov et al. | 73/54.28 |
| 2004/0131500 A1 * | 7/2004 | Chow | 422/72 |
| 2005/0032200 A1 * | 2/2005 | Sun et al. | 435/286.7 |
| 2005/0202566 A1 * | 9/2005 | Frojmovic | 436/63 |
| 2006/0068492 A1 | 3/2006 | Choi et al. | |
| 2006/0223049 A1 * | 10/2006 | Dancu et al. | 435/1.2 |
| 2008/0038816 A1 | 2/2008 | Ting et al. | |
| 2008/0145922 A1 | 6/2008 | Lehmann et al. | |
| 2009/0075360 A1 | 3/2009 | Ho et al. | |

OTHER PUBLICATIONS

Dai et al. "Distinct Endothelial Phenotypes Evoked by Arterial Waveforms Derived from Artherosclerosis Susceptible and Resistant Regions of Human Vasculature," PNAS, vol. 101, No. 41, Oct. 12, 2004, pp. 14871-14876.

International Search Report for PCT Application No. PCT/US2010/021002, mailed Jun. 18, 2010, 4 pages.

Written Opinion for PCT Application No. PCT/US2010/021002, mailed Jun. 18, 2010, 4 pages.

* cited by examiner

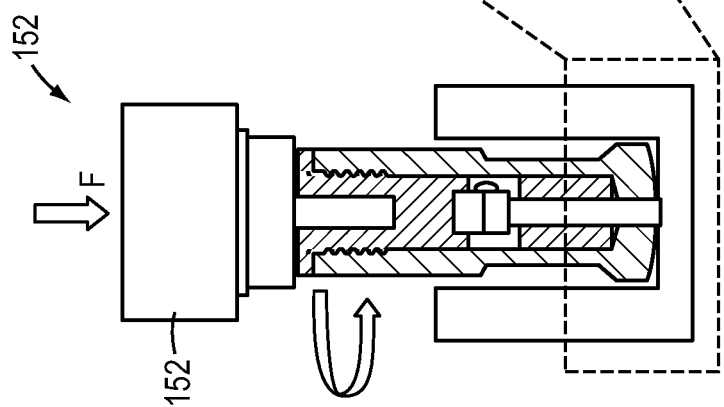
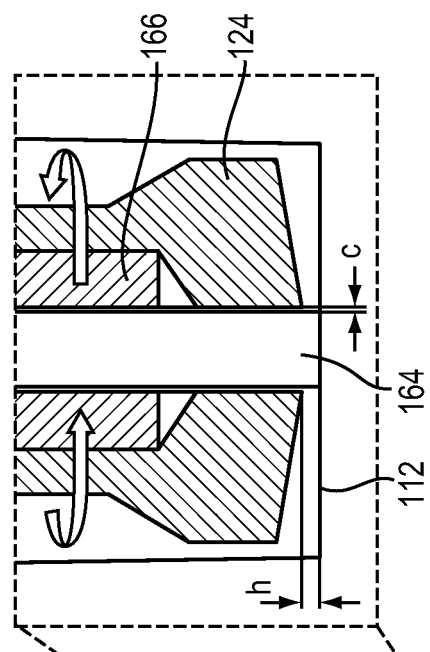
FIG. 4C
FIG. 4D

HIGH-THROUGHPUT BIOLOGICAL SCREENING

CROSS-REFERENCE TO RELATED APPLICATION

This application claims priority to and the benefit of, and incorporates herein by reference in its entirety, U.S. Provisional Patent Application No. 61/145,037, which was filed on Jan. 15, 2009.

TECHNICAL FIELD

In various embodiments, the present invention relates to high-throughput biological screening and, in particular, to high-throughput flow systems and methods of applying hemodynamic waveforms to cells located therein.

BACKGROUND

Drug discovery often involves laborious biological testing of candidate compounds by, for example, exposing them to samples of tissue that exhibit the disorder to be treated. For example, in screening candidate compounds for efficacy against atherosclerosis, it is common to subject cultured endothelial cells to shear stress, which affects the growth and behavior of adherent cultured cells. For example, the applied shear stress can mimic circulatory conditions encountered by the cells in vivo. In a conventional "single-well" system, a single motor-cone assembly is arranged in a single-well plate with cultured endothelial cells and is actuated to impart a shear-stress pattern to the cells. One disadvantage of this approach is that the time required to screen compounds may be impractically long; since each shear condition to be studied typically requires replicates (i.e., multiple tests for each shear condition), a multiplicity of shear conditions is generally required to carry out high-throughput screening in a meaningful manner, and multiple compounds/reagents under investigation must be investigated serially.

Accordingly, a need exists for a high-throughput flow system and for related methods of performing biological screening.

SUMMARY OF THE INVENTION

Embodiments of the present invention utilize unit structures known as mini-shear machines ("MSMs"), each of which comprises a cone controlled by a variable-speed precision motor in one of an array of wells. For example, the wells may each be a single well of a multi-well plate, or may instead be an array of discrete wells—e.g., miniature cuvettes in a rack. A multiplicity of these unit structures may be assembled into a large-scale system such that one separately-actuatable MSM is positioned within each well of the multi-well plate.

An advantage of this approach over conventional techniques is the ability to precisely control shear and introduce shear stress waveforms in a multitude of cell-culture wells in parallel for high-throughput screening. A single experiment involving replicates, multiple shear conditions, and multiple compounds that can be done in one day using the approach described herein might require upwards of one year using existing technology.

In general, in one aspect, embodiments of the invention feature a high-throughput flow system for use with an array of wells. The system includes an array of mechanical tips that each correspond to one of the wells, an interface facilitating the necessarily precise positioning each tip within its corresponding well, and a separate driver associated with each tip for driving the tip to impart a shear stress pattern in its corresponding well. The shear stress patterns may mimic physiological hemodynamic waveforms present in the circulatory system of an organism (e.g., a human, a mouse, etc.), such as atheroprotective waveforms, atheroprone waveforms, and/or waveforms that promote, increase or direct cell differentiation. The cells themselves may be epithelia osteoblasts or osteocytes, blood cells, stem cells, etc.

In general, in another aspect, embodiments of the invention feature a method of applying hemodynamic waveforms to an array of wells. Each of the wells is at least partially filled with a liquid (e.g., a cell culture medium) and contains biological cells. In accordance with the method, a separate mechanical tip is disposed in each of the wells. Each mechanical tip is separately rotated to transmit a shear force through the liquid to the cells. The shear forces may create shear stress patterns that again mimic physiological hemodynamic waveforms present in the circulatory system of an organism (e.g., a human, a mouse, etc.), such as atheroprotective waveforms, atheroprone waveforms, and/or waveforms that promote, increase or direct cell differentiation.

In various embodiments of these aspects of the invention, the shear stress patterns have a magnitude of up to 35 dynes/$cm^2$. The shear stress patterns may include temporal and spatial variations. For example, the shear stress patterns may be oscillatory shear stress patterns. Alternatively, the shear stress patterns may be steady shear stress patterns. In addition, each mechanical tip (whose bottom surface may optionally have a flat center and an overall conical shape) may be positioned so as not to contact a surface of its corresponding well and/or so as not to contact any of the cells grown therein. The cells may be, for example, endothelial cells, stem cells, or any other type of mechano-responsive cells.

In one embodiment, at least one of the drivers associated with a mechanical tip is a variable-speed precision motor, such as a stepper motor. The high-throughput flow system may further include means for regulating a level of carbon dioxide and or oxygen in an environment surrounding the well array and means for controlling the temperature and humidity in that environment. For example, the well array may be positioned within a temperature-controlled fluid bath, and a heater may be employed to control the temperature of the fluid bath. In one implementation, the temperature of the fluid bath is maintained at approximately 37° C. In one specific embodiment, the well array includes 96 wells defined within a well plate.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4C is a schematic cutaway view of an MSM as shown in FIG. 4B;

FIG. 4D is an enlarged schematic cutaway view of a portion of the MSM shown in FIG. 4C;

DESCRIPTION

Figure 1:
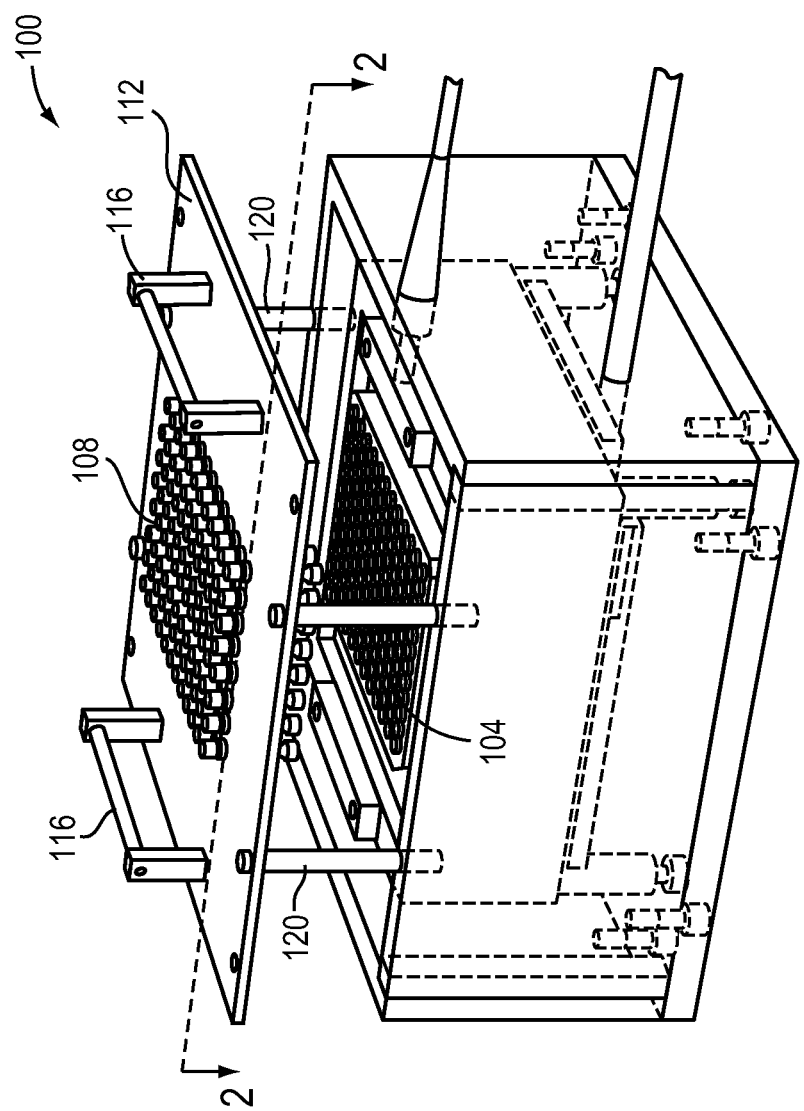
FIG. 1 schematically illustrates a high-throughput flow system in accordance with one embodiment of the invention.

In various embodiments, the present invention relates to high-throughput biological screening. FIG. 1 depicts a high-throughput flow system 100 in accordance with one embodiment of the invention. As illustrated, the high-throughput flow system 100 includes an array of wells 104 and an array of mechanical tips 108. As further described below with respect to FIG. 3, each mechanical tip 108 may in fact be part of, and be controlled by, a larger MSM. Each mechanical tip 108 corresponds to one of the wells 104. More specifically, an interface 112 is coupled to the array of tips 108 and is employed to position each tip 108 within its corresponding well 104. For example, the interface 112 may be, as illustrated, a single motor plate. In one embodiment, the single motor plate 112 is machined from stainless steel to give it a high-precision flatness. A pair of handles 116 may be employed to lower and raise the single motor plate 112, and guide posts 120 may be employed to steer the plate 112 and facilitate proper alignment with the wells 104.

Figure 2:
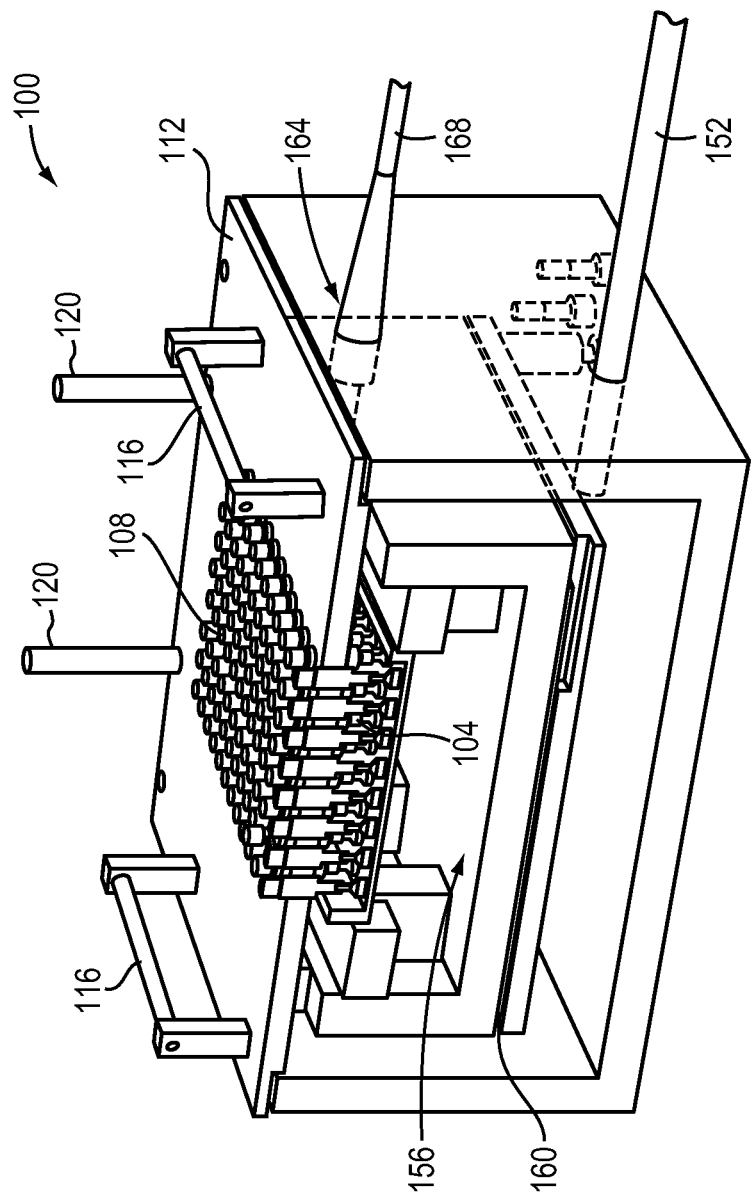
FIG. 2 is a schematic cutaway view of the high-throughput flow system of FIG. 1, along the line 2-2.

As illustrated in FIG. 2, the motor plate 112 may be clamped down to simultaneously seat each of the tips 108 within its corresponding well 104. Advantageously, by precisely machining the motor plate 112 and coupling it to the array of mechanical tips 108, the tips 108 may be raised or lowered in unison so as to be precisely located at the same height within its corresponding well 104. In this way, each tip 108 may be actuated, as further described below, to impart substantially the same shear stress pattern to biological cells within each well 104. As such, replicates of the same shear stress pattern may be studied in parallel, vastly reducing the overall experiment time.

In one embodiment, the array of wells 104 is defined within a well plate. For example, 96 individual wells 104 may be individually formed (e.g., machined) within the well plate. More generally, however, any number of wells 104 may be formed within the well plate. For example, a multi-well configuration of 24 wells or of 384 wells may be employed. The well plate may be, for example, any of the commercially available well plates manufactured by Nunc, a division of Thermo Fisher Scientific, Inc. In addition, microfluidic channels may optionally be employed to address any one or more of the individual wells 104 to facilitate the introduction therein of cells, cell culture medium, and/or test compounds (e.g., candidate drugs, small molecules, and/or genes), as further described below.

Figure 6:
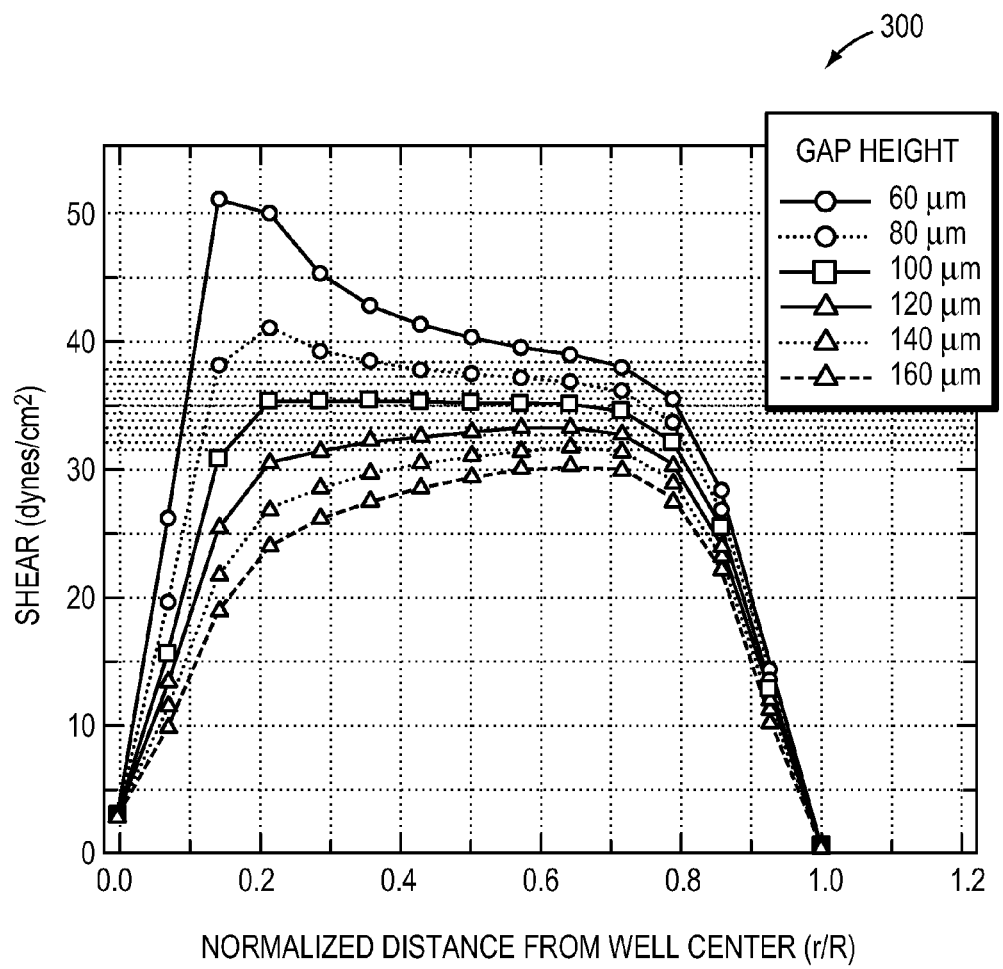
FIG. 6 is a graph illustrating the shear distributions on the well surface depicted in FIG. 3 for various gap heights between the illustrated rotatable cone and well surface.

In one embodiment, as further described below with reference to FIG. 6, each tip 108 is actuated to impart, within its corresponding well 104, a shear stress pattern that mimics a waveform—e.g., a physiological hemodynamic waveform—present in the circulatory system of an organism, such as a human or mouse. For example, the waveforms may be atheroprotective waveforms, atheroprone waveforms, and/or waveforms that increase or direct the differentiation of cells, e.g., stem cells. This enables the behavior of the cells and/or test compounds to be investigated under different flow conditions. Each shear stress pattern may include temporal and spatial variations. For example, the shear stress patterns may be oscillatory shear stress patterns. Alternatively, the shear stress patterns may be steady shear stress patterns.

Figure 3:
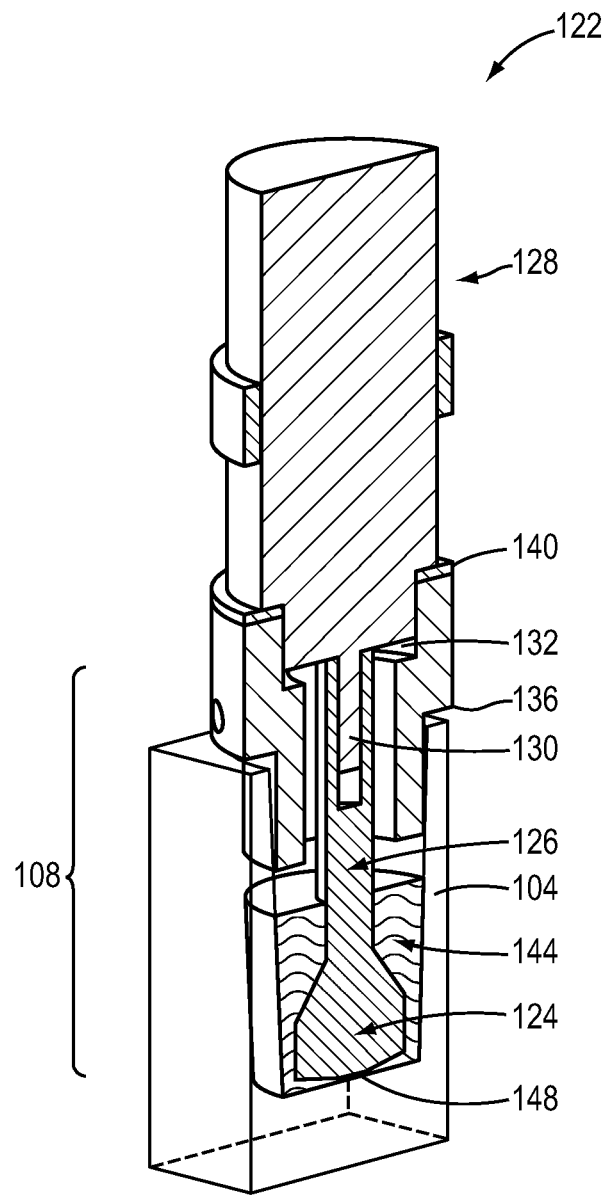
FIG. 3 is a schematic cutaway view of a single MSM in accordance with one embodiment of the invention.

With reference to FIG. 3, each mechanical tip 108 may in fact be part of, and be controlled by, a larger MSM 122. As illustrated, the tip 108 may include a rotatable cone 124 and an elongate shaft 126 that extends therefrom. The shaft 126 couples to a motor 128 (e.g., a variable-speed precision motor, such as a stepper motor) of the MSM 122. In one embodiment, the tip 108 is coupled to a motor shaft 130 by close-slip fit and glue. There are a number of ways to position the tip 108 axially with high precision. In one exemplary implementation, one or more shim washers 132 are placed on the motor axis between the motor 128 and tip 108. The number and thickness of the washers 132 controls the axial position of the tip 108 relative to that of the motor 128. With shims 132 that are 10 μm thick, the axial tip 108 position may be controlled within 10 μm. Furthermore, the tip 108 may be held in place by a jig while adhesive bonds the elongate shaft 126 of the tip 108 to the motor shaft 130. Tip 108 position may be monitored during assembly using either physical tools, such as a drop tester, or optical tools.

Using these high-precision techniques for fixing the axial position of the tip 108, and because shear-distribution simulations (discussed below with reference to FIG. 5) provide a guide for the sensitivity of shear errors with tip 108 height, it is possible to compensate for slight imprecision in well 104 depths of common well plates, and subsequently place bounds on the total margin of error.

Advantageously, by precisely fixing the axial position of the tip 108, the cone 124 (and elongate shaft 126) may be positioned so as not to contact a surface of its corresponding well 104 or any of the biological cells cultured therein. Alternatively, different approaches may be employed. For example, the cone 124 may in fact be allowed to touch a surface of its corresponding well 104. In that case, an additional rotational bearing may be employed to reduce friction. A mechanism may also be used to allow for adjustable height, with optical or mechanical feedback.

In one embodiment, with reference still to FIG. 3, a motor collar 136, which may screw onto motor threads, acts as an adapter so that the MSM 122 sits snugly in its corresponding well 104. Above the collar 136, the motor plate 112 (not shown in FIG. 3) couples to the motor 128. Pushing the motor plate 112 down, as described above, then seats the collar 136 onto the well 104. Optionally, a gasket 140 may be placed between the collar 136 and the motor plate 112 to ensure that the collar 136 is pushed flush against the top of the well plate when the motor plate 112 is lowered. Controlling the axial position of the tip 108 relative to the collar 136, as described above, and pushing the collar 136 securely against the well plate together ensure that the distance between the cone 124 of the tip 108 and the surfaces of the well 104 is controlled. Of course, other arrangements are possible. For example, if the tip 108 height is controlled by allowing the cone 124 to contact a bottom surface of the well 104, the collar 136 need not securely contact the well plate.

As mentioned, embodiments of the MSM 122 may be designed to interface with an existing well plate, such as a 96-well plate manufactured by Nunc. Alternatively, it is possible to use custom-manufactured well plates. These plates may incorporate physical features to secure the radial and axial positions of the cone 124 to maintain radial, and optical alignment marks to monitor cone position.

In some embodiments, hemodynamic shear stress waveforms are applied within all the wells 104 in a well plate by arraying one MSM 122 for each well 104. In general, there is one motor 128, tip 108, and collar 136 for each well 104. The gasket 140 between the motor plate 112 and collar 136 ensures that all collars 136 are seated in their individual wells 104.

Figure 4A:
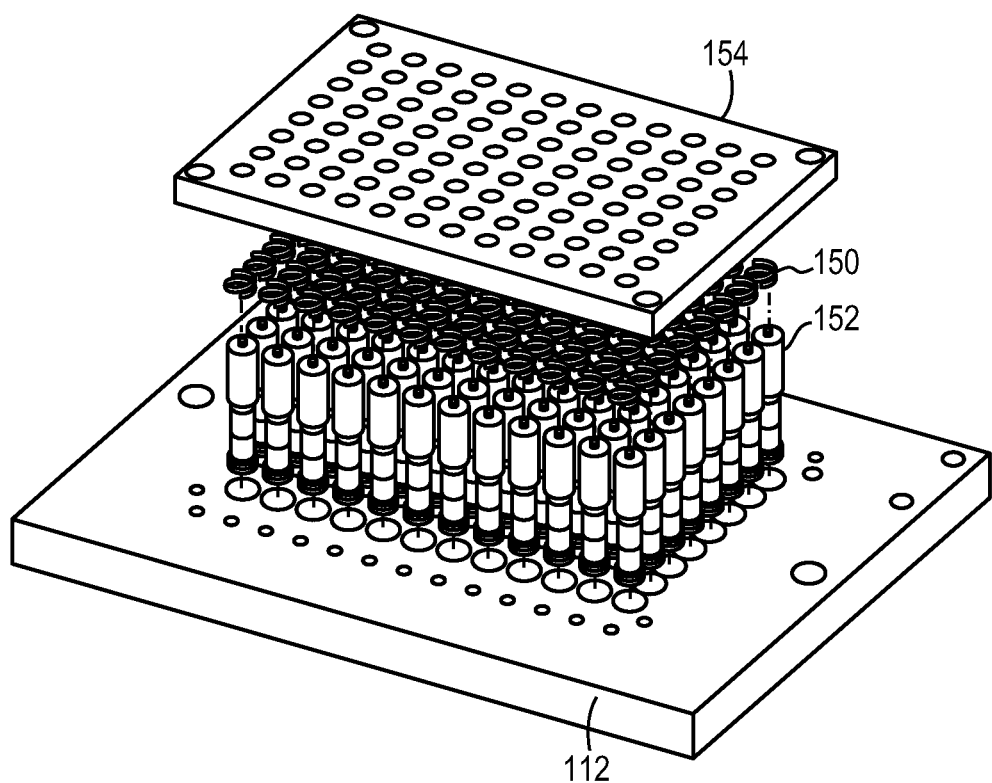
FIG. 4A is an exploded view of another embodiment of an MSM array, in which the MSM are spring-loaded.
Figure 4B:
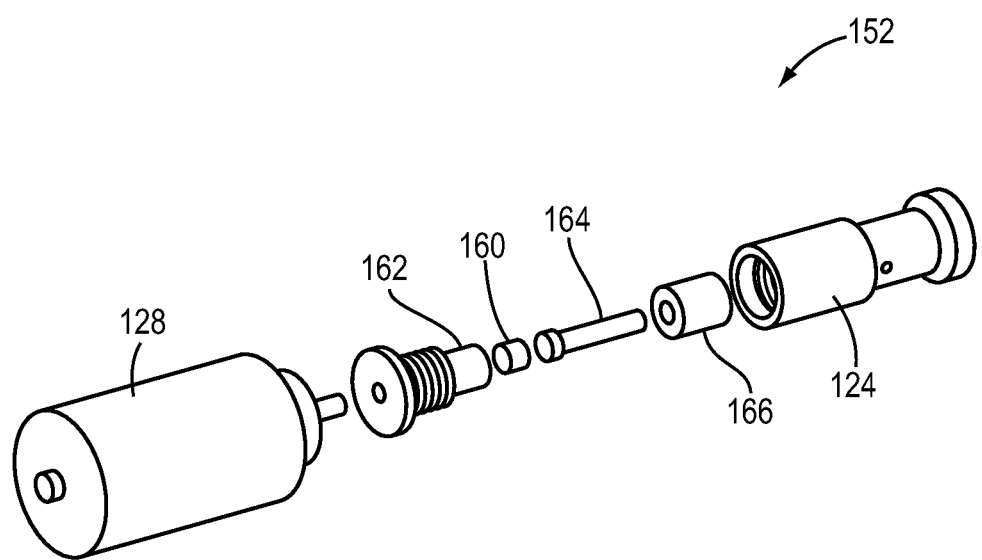
FIG. 4B is an exploded view of the MSM as shown in FIG. 4A.

The shear stress pattern delivered to the biological cells adhered to the well bottom 104 is critically dependent on the distance, h, between the rotating cone 124 of the tip 108 and the bottom of the wells 104 of the well plate. Given typical dimensions of the device and the hemodynamic settings in which it may be used, a 1 μm error in h may produce a 1% error in the shear stress applied. To enforce an exact and consistent distance h, a post of precise length may be incorporated to the MSM as shown in FIGS. 4A-4D. With reference to FIG. 4A, a spring 150 is disposed over each of the MSMs 152, and a spring plate 154 urges the springs 150 against the tops of MSMs 152. As shown in FIG. 4B, each of the MSMs 152 includes a motor 128, a jewel bearing 160 between a shaft seat 162 (which receives the shaft of motor 128) and the post 164. The cone 124 is secured (e.g., via threads) to the shaft seat 162, and the post 164 passes through a TEFLON bearing 166 and the cone 124. With reference to FIGS. 4C and 4D, the spring associated with MSM 152 urges the post 164 (via the motor 128, shaft seat 162 and bearing 160) against the floor of the corresponding well in plate 112. This enforces the desired distance h, which is established by the extension of the post 164 beyond the bottom of the cone 124. In some embodiments, a clearance space c separates the inner wall of the cone 124 from the post 164 to permit free rotation of the cone around the post; similarly, jewel bearing 160 facilitates free rotation of the shaft seat 162 (and, hence, the cone 124) relative to the top of the post 164. This self-adjusting configuration maintains a constant distance between cone and well bottom despite variations in commercially available well plates. Furthermore, the floor of each well has a small recess to receive the post 164 therein in order to enforce radial alignment (i.e., concentricity) between the cone 124 and the well wall; in this case, the post 164 has extra length corresponding to the depth of the recess.

In another embodiment, a precise and accurate distance h is achieved by attaching a precision-machined sleeve to the outer body of each motor and spring loading the motors so the bottom edge of each sleeve is held against the floor of the corresponding well. Each cone rotates within its surrounding sleeve, and the distance between the bottom of the cone and the bottom of the sleeve is h. When the sleeve rests against the bottom of the well, it captures a portion of the well volume. The cells cultured within this sleeve experience uniform shear according to their radial position and are not subject to concentricity error because the inner walls of the sleeve define the boundary of the rotating flow. Outside the sleeve, in the excess medium between the sleeve and the well wall, no cells are cultured and no measurements made. The sleeves may, for example, be machined from glass to enable aggressive cleaning procedures and to ensure biocompatibility. Glass also provides relatively low thermal conductivity to resist transfer of heat from motors to the cultured cells. Using this configuration, each cone will automatically adjust to the desired distance h above the well bottom to within, for example, ±5 μm. Additionally, the sleeve defines new sidewalls in the well, such that the sleeves are concentric to within, for example, 2% of the well diameter.

Other methods for applying shear in an array are possible. For example, fewer motors 128 may be used with mechanical linkages, such as pulleys or chains, so that each motor 128 drives multiple cones 124 in parallel. The cones 124 may alternatively be driven by non-mechanical methods, including electromagnetic or pneumatic actuation. The high-throughput flow system 100 can be adapted to accommodate a wide variety of commercially available well plates, custom-built well plates, and well plates with different dimensions and numbers of wells 104.

A general strategy for applying hemodynamic waveforms to cultured cells may involve the following steps. First, each well 104 of the array of wells 104 may be at least partially filled with a liquid cell culture medium 144, and cells may then be grown therein as a single layer. Then, the cone 124 of each MSM may be precisely located in each well 104 to a predetermined height above the cell surface. Finally, each cone 124 may be separately driven (e.g., rotated) by its respective motor 128, thereby transmitting a shear force through the liquid cell culture medium 144 to the cells. The cells may be any type of mechano-responsive cells, such as, for example, endothelial cells and/or stem cells.

Figure 5:
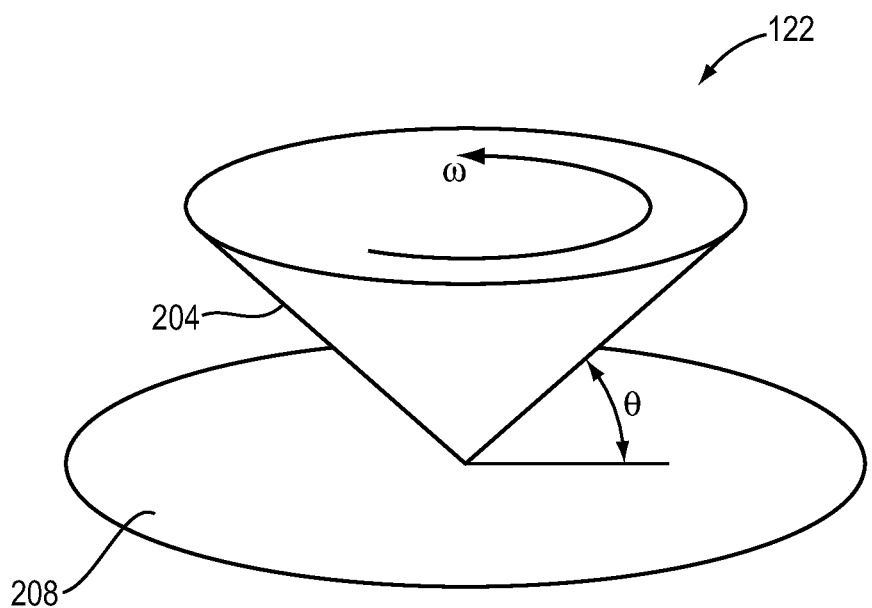
FIG. 5 schematically illustrates a simplified cone-plate shear machine in accordance with one embodiment of the invention.

With reference now to FIG. 5, a large-scale (approximately 150-mm diameter) cone-and-plate shear machine 200 has been used to apply hemodynamic waveforms to cultured human endothelial cells in the context of several specific experimental goals. The cone 204 in the large-scale machine 200 is conical. With this geometry, the shear is constant over the surface of a dish 208, and the magnitude τ of this shear may calculated according to the equation:

$$\tau = \frac{\mu \Omega}{\tan \theta}$$

where μ is the viscosity of the fluid in the dish 208, Ω is the rotational speed of the cone 204, and θ is the angle between the cone 204 and the dish 208, as illustrated in FIG. 5.

Embodiments of the invention, as described above, utilize a miniaturized MSM. Similar to the larger device 200, the MSM 122, 152 comprises a motor 128 driving a rotating tip 108. In one embodiment, the MSM has a combination of tip 108 shape and motor 128 that can impart shear stress patterns having magnitudes of up to 35 dynes/cm$^2$. The equation above shows that delivering high shear requires low angle θ and high rotational speed Ω. In various embodiments, to avoid scraping the well 104 surface or attached cells (and thereby slowing the rotational speed Ω of the tip 108), the tip 108 of the MSM is designed so that it does not contact the interior surface of the well 104. For example, with renewed reference to FIG. 3, a center 148 of the bottom surface of the rotatable cone 124 may in fact be flat, while the rest of the cone's bottom surface has a conical shape. In other embodiments, the tip 108 does contact the surface of its corresponding well 104, or a different tip 108 shape is employed.

The analytical expression for shear in the above equation assumes a perfect cone 204, and, thus, this expression is generally imprecise for the embodiment of the MSM design depicted in FIG. 3. Instead, to calculate exact shear distributions in the MSM 122, a numerical method may be employed. As an example, a numerical simulation of the fluid shear forces resulting from rotation of the tip 108 having the shape depicted in FIG. 3 has been performed. The simulation results confirmed that a constant shear of approximately 35 dynes/$cm^2$ may be delivered over the majority of the well 104 surface with a cone 124 angle θ of approximately 10° and a rotational speed Ω for the cone of approximately 35 rotations/sec.

One motor 128 that can deliver this rotational speed, and is sufficiently small to be arrayed over a well plate as dense as the common 96-well system manufactured by Nunc, is the Arsape AM-0820 high-precision micro-stepper motor available from MicroMo Electronics, Inc. of Clearwater, Fla. This motor has a step resolution of 18 degrees, with the capability to divide each step into 256 sub-steps. In addition, the drag force of the fluid 144 on the cone 124 at the cone's maximum speed is within the torque specifications of the Arsape motor, meaning that the Arsape motor is also able to deliver adequate torque. Optionally, other commercially available variable-speed precision motors, or combinations thereof, may be employed instead of, or in combination with, the Arsape motor.

Ordinarily, the distance between the cone 124 and the well 104 surface is tightly controlled in order to precisely deliver the desired hemodynamic shear values. A simulation has also been performed to investigate the allowable error in the height of the tip 108. The graph 300 of FIG. 6 depicts the shear distribution across the well 104 surface given a 100 μm desired height offset, and the subsequent shear distributions given errors in either direction. As can be seen, a vertical error of up to 40 μm above the desired offset gives a constant level of shear over the majority of the well 104, with a −10% error in the magnitude. Advantageously, the Arsape motor possesses precision bearings, specifying a sub-micron axial error, and accordingly does not introduce any significant error in applied shear.

Figure 7:
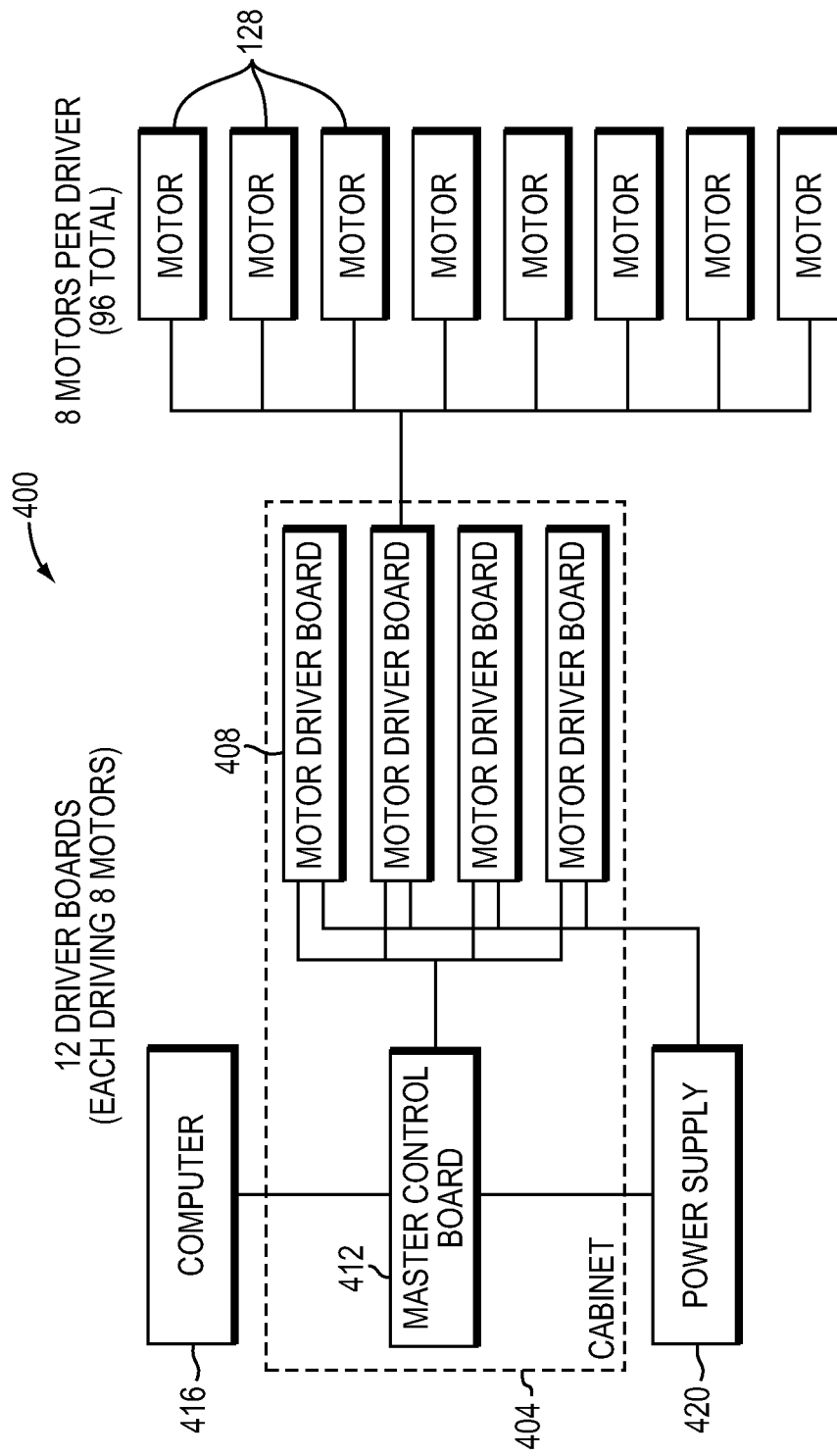
FIG. 7 depicts one embodiment of the electronics for the high-throughput flow system of FIG. 1.

FIG. 7 depicts one embodiment of the electronics 400 for the high-throughput flow system 100. Of course, other electronic control layouts and strategies are possible, and the layout depicted in FIG. 7 is thus provided by way of example only and is non-limiting. As depicted, the electronics 400 include circuitry, hardware, and software for driving each of the MSM 122 motors 128 with specific velocity profiles. In one embodiment, a single electronics cabinet 404 houses two main components: i) a stacked series of 8-channel motor driver boards 408, each capable of driving up to eight motors 128 with, for example, A3967 microstepping drivers manufactured by Allegro MicroSystems, Inc. of Worcester, Mass.; and ii) a master control board 412 that commands the motor driver boards 408 and that interfaces with a computer 416 (e.g., a personal computer) via, for example, an RS-232 serial port.

Control lines running from the master control board 412 to each motor driver board 408 may also be enclosed within the electronics cabinet 404 and carry standard registered jack ("RJ") connectors. RJ connectors may also be used as the output interfaces from the 8-channel motor driver boards 408 to the eight motors 128 they drive. As such, for an exemplary 96-well system, 96 RJ inputs appear on the outside of the electronics cabinet 404—one RJ input for each motor 128 wire.

In one embodiment, the master control board 412 is equipped with a PIC microcontroller manufactured by Microchip Technology, Inc. of Chandler, Ariz., enabling the master control board 412 to store various velocity profiles that may be loaded into it from, for example, the computer 416. The full motor driver system 400 may be stand-alone, and after programming the master control board 412 with the velocity profiles, the master control board may be disengaged from the computer 416 to autonomously run the motors 128 with start, stop, and pause commands. Finally, an external power supply (e.g., a 12V DC power supply, such as the VPM-S300 manufactured by V-Infinity of Tualatin, Oreg.) may be used to power the electronics 400.

Figure 8:
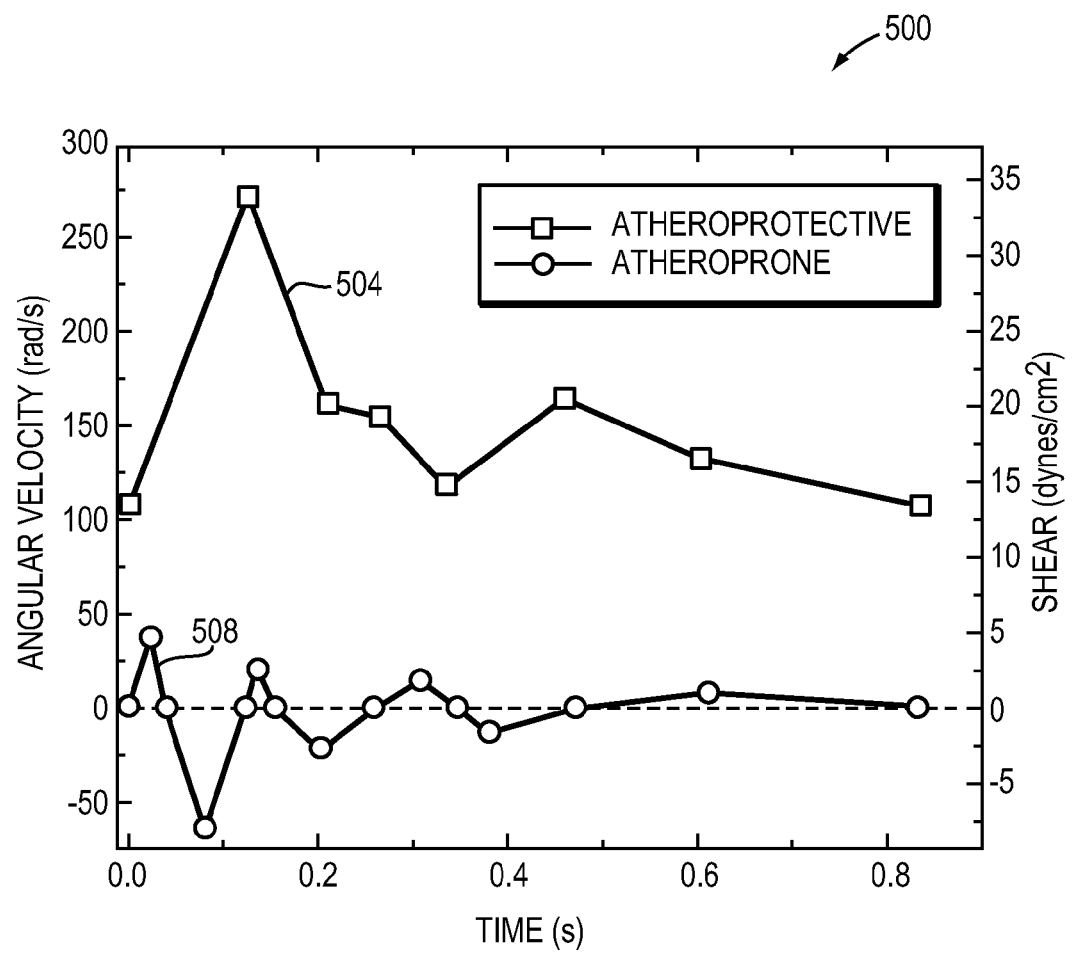
FIG. 8 is a graph illustrating exemplary atheroprotective and atheroprone shear stress waveforms.

Any type of waveform, for example any physiological hemodynamic waveform that is capable of influencing cell behavior along different directions and/or any other arbitrarily derived waveform, may be loaded into the master control board 412. Exemplary shear profiles that may be loaded into the master control board 412 include, but are not limited to: i) an atheroprotective waveform; ii) an atheroprone waveform; iii) a constant 12 dynes/$cm^2$ waveform; iv) a constant 5 dynes/$cm^2$ waveform; v) an arbitrarily-oscillatory waveform; vi) a waveform having a pseudo-static profile consisting of a single motor step every 30 seconds; and vii) a waveform that increases stem cell differentiation. Atheroprotective and atheroprone waveforms are shear stress patterns that are representative of atherosclerosis-resistant and atherosclerosis-susceptible regions in the human carotid artery, respectively. FIG. 8 is a graph 500 depicting the discretized forms of a single cycle of an atheroprotective profile 504 and an atheroprone profile 508. The discretized, angular velocity time points may be programmed into the master control board 412.

Generally, cell culture should be performed in an environment where carbon dioxide, temperature, and humidity are all tightly regulated. Accordingly, in one embodiment, with reference again to FIG. 2, carbon dioxide is pumped into the environment surrounding the array of wells 104 along a line 152 from an external source using, for example, a mixed air pressurized tank and flow regulator available from Airgas, Inc. of Radnor, Pa. In addition, the temperature and humidity in the environment surrounding the array of wells 104 may be controlled by, for example, positioning the well plate within a temperature-controlled fluid bath 156 that is isolated from the outside environment. Lexan walls may form the outer case of the fluid bath 156. In one embodiment, the fluid bath 156 is heated with a heater 160, such as a 5×6 inch 2.5 Watt/$in^2$ flexible silicone fiberglass insulated heater (e.g., Part # SRFG available from Omega Engineering, Inc. of Stamford, Conn.). The temperature of the heater 160 may be controlled by using a feedback loop that includes temperature measurement with a thermocouple 164 (e.g., Part # KMTSS-040U-6 available from Omega Engineering, Inc. of Stamford, Conn.), and heater input power adjustment with a ramp/soak temperature controller (e.g., Part #CN74030 available from Omega Engineering, Inc. of Stamford, Conn.). The temperature of the fluid bath 156 may be set in order to maintain a temperature of, for example, approximately 37° C. in each well 104.

In one embodiment, the evaporation rate in the fluid bath 156 is about 80 ml/hr/$cm^2$. At this rate, the fluid bath 156 can be employed for approximately 24 hours before its fluid level drops to a point where it is no longer contacting the well plate. In case this duration is not long enough, the fluid bath 156 may also include a connection 168 to an external fluid source so that the fluid level within the fluid bath 156 can be adjusted without having to open the high-throughput flow system 100.

As will be appreciated by one of ordinary skill in the art, several alternatives exist for controlling the environment within the wells 104. For example, air temperature and humidity may be controlled in a separate device and then be pumped into the environment surrounding the array of wells 104, while the temperature of individual wells 104 can be controlled by applying heat sources directly to the well plate. Alternatively, an enclosure for the entire high-throughput flow system 100 may be used to control both the temperature and humidity.

In practice, the high-throughput flow system 100 may be operated to generate a variety of different flow conditions (e.g., both healthy flow conditions and diseased flow conditions) and the behavior of different types of mechano-responsive cells (e.g., endothelial, stem, etc.) may be investigated under those different flow conditions. Moreover, candidate drugs, small molecules, siRNAs, shRNAs, microRNAs, and/or genes may be introduced to the cells to test their efficacy in treating certain diseased flow conditions. For example, high-throughput screens may be employed to identify, without limitation: i) genes (e.g., via cDNA libraries, shRNA libraries, siRNA libraries, microRNAs, etc.) and/or small molecules that are capable of conferring vascular atheroprotection, and might thus be used for the treatment of atherosclerosis and/or other inflammatory diseases; ii) genes (e.g., via cDNA libraries, shRNA libraries, siRNA libraries, microRNAs, etc.) and/or small molecules that are capable of inhibiting the expression of atherosclerosis-susceptible genes, and might thus be used for the treatment of atherosclerosis and/or other inflammatory diseases; iii) genes (e.g., via cDNA libraries, shRNA libraries, siRNA libraries, microRNAs, etc.) and/or small molecules that are capable of increasing the differentiation of embryonic stem cells into blood components, and might thus be used in the treatment of hematopoietic disorders; iv) genes (e.g., via cDNA libraries, shRNA libraries, siRNA libraries, microRNAs, etc.) and/or small molecules that are capable of regulating cellular differentiation (e.g., epithelial, osteoclast, osteoblasts, and cardiac myocytes); and v) small molecules that are capable of disrupting vascular function and/or inducing endothelial toxicity, and might thus be used for assessing drug toxicity specific to the vascular endothelium with implications for other systems or organs.

Advantageously, the large-scale, high-throughput parallel-processing flow system 100 enables the direct comparison between and among a large number of cell populations at the same time, and therefore reduces the time needed to obtain such high-throughput screening data on drug discovery, drug safety, and other applications.

EXAMPLES

An embodiment of the above-described high-throughput flow system 100 was tested using a 96-well Nunc plate. The system 100 included three of the twelve motor driver boards 408 in order to apply multiple shear stress waveforms, as well as no shear, to three entire columns of 8 wells each. Biological readouts were used to evaluate both the ability of the MSM 122 to evoke endothelial cell responses expected with shear application, and also consistency between multiple MSMs 122. The biological readouts included endothelial cell morphology, actin stress fiber formation, and KLF2 gene expression.

Figure 9:
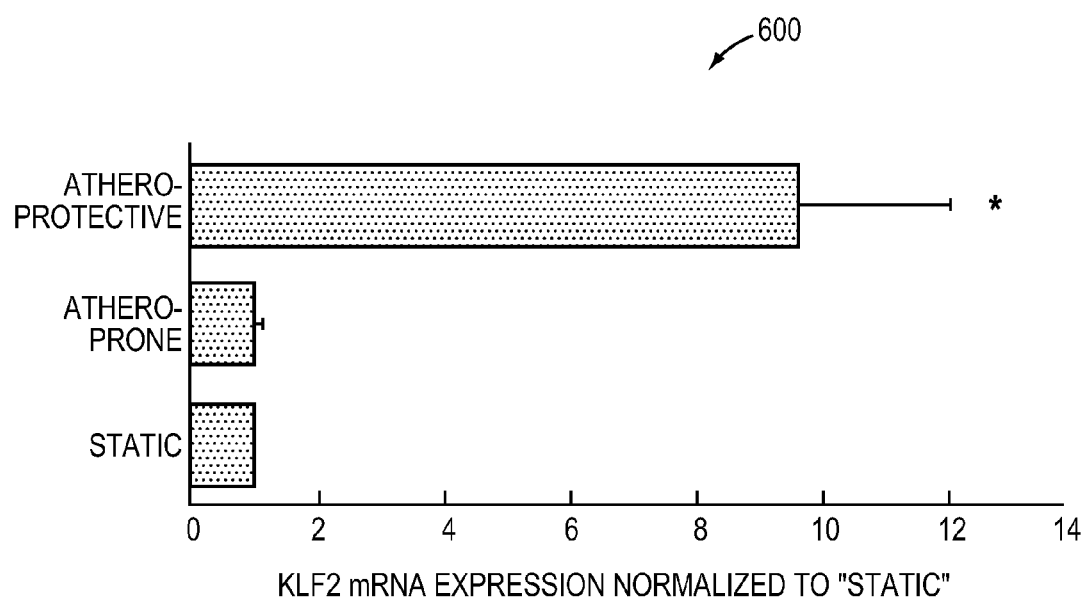
FIG. 9 is a graph illustrating the level of KLF2 mRNA gene expression induced in human umbilical vein endothelial cells under three different flow conditions.
Figure 10:
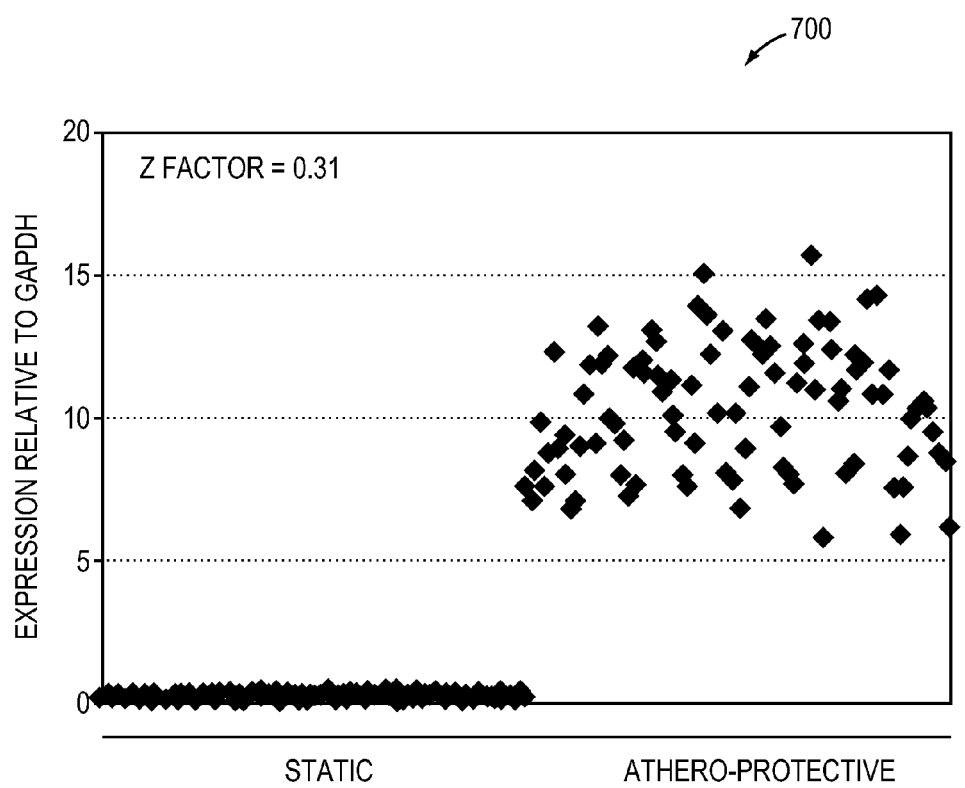
FIG. 10 is a graph illustrating the measurement of KLF2 gene expression in human umbilical vein endothelial cells from each well of a static and atheroprotective flow plate.

More specifically, human umbilical vein endothelial cells ("HUVEC") were plated in select wells of a 96-well Nunc plate at a density of 60,000 cells/cm$^2$ and maintained in a complete growth medium for 24 hours. The cells were then washed and exchanged for shear medium (i.e., complete growth medium+2% dextran in order to increase the viscosity to 2.2 cP). The 96-well plate was then placed in the environmentally controlled high-throughput flow system 100 and the MSMs 122 were positioned in their corresponding wells 104. The HUVEC were allowed to recover for 30 minutes before initiating either an atheroprotective waveform, an atheroprone waveform, or a static (i.e., no flow) waveform condition. The HUVEC subjected to the atheroprotective waveform for 24 hours, as compared with the atheroprone waveform and static control cells, displayed aligned morphology under phase contrast, as well as actin stress fiber formation based on an Alexa488 phalloidin staining. Furthermore, measurement of KLF2 mRNA gene expression across the three conditions resulted in, as illustrated in the graph 600 of FIG. 9, a 10-fold induction in HUVEC exposed to the atheroprotective waveform as compared to the atheroprone and static control waveforms, which is a level that is consistent with previously published data. Moreover, this induction was consistent across the measured samples for each flow condition, as is evidenced by the standard error bars in FIG. 9.

Next, a 96-well test was performed by subjecting the HUVEC in a complete 96-well system to atheroprotective flow for 24 hours and comparing the resulting KLF2 mRNA gene expression with static control cells also plated in a 96-well plate. As illustrated in the graph 700 of FIG. 9, this comparison revealed that KLF2 gene expression is induced in endothelial cells exposed to the atheroprotective waveform across the entire 96-well system.

Furthermore, a statistical characterization of the assay was performed by calculating the Z-factor, a measure of power for a particular high-throughput flow system 100, using:

$$Zfactor = 1 - \frac{3(\sigma_p + \sigma_n)}{|\mu_p - \mu_n|},$$

where $\sigma$ is the sample standard deviation and $\mu$ is the sample mean of the positive (subscript 'p') and negative (subscript 'n') conditions. For the purposes of this test, the atheroprotective waveform represented the positive condition and the static control represented the negative condition. A Z-factor of 0.31 was calculated for these conditions, indicating that the high-throughput assay has sufficient power for conducting a high-throughput screen.

Based on these test results, the implementation of the high-throughput flow system 100 was confirmed to evoke the expected endothelial cell responses when exposed to defined shear stress waveforms, and it was also confirmed that these responses can be reproduced across the entire 96-well system and while using multiple waveforms simultaneously.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A high-throughput flow apparatus for use with an array of wells, the apparatus comprising:

an array of mechanical tips each corresponding to one of the wells;

an interface for positioning each tip within its corresponding well;

a separate sleeve mechanically coupled with each tip and extending beyond a distal end thereof, each sleeve thereby being adapted to contact a floor of its corresponding well and to maintain a predetermined distance between its tip and the floor of a testing chamber, wherein the testing chamber is defined by a volume captured within an inner diameter of the sleeve, each tip rotatable within its corresponding sleeve; and a driver associated with a tip for driving the tip within its respective separate sleeve to impart a shear stress pattern in its corresponding testing chamber.

2. The apparatus of claim 1, wherein the shear stress pattern mimics a physiological hemodynamic waveform present in the circulatory system of an organism.

3. The apparatus of claim 2, wherein the physiological hemodynamic waveform comprises at least one of an atheroprotective waveform, an atheroprone waveform, or a waveform that increases stem cell differentiation.

4. The apparatus of claim 2, wherein the organism is at least one of a human or a mouse.

5. The apparatus of claim 1, wherein the shear stress pattern comprises at least one of a steady shear stress pattern or an oscillatory shear stress pattern.

6. The apparatus of claim 1, wherein the shear stress pattern comprises temporal and spatial variations.

7. The apparatus of claim 1, wherein the shear stress pattern has a magnitude of up to 35 dynes/cm$^2$.

8. The apparatus of claim 1, wherein each tip does not contact a surface of its corresponding well.

9. The apparatus of claim 1, wherein each of the wells comprises a feature interfacing with a complementary feature of the corresponding mechanical tip for maintaining radial alignment between the tip and an interior wall of the well.

10. The apparatus of claim 1, wherein a bottom surface of each tip has a flat center and an overall conical shape.

11. The apparatus of claim 1, wherein the driver comprises a variable-speed precision motor.

12. The apparatus of claim 11, wherein the variable-speed precision motor is a stepper motor.

13. The apparatus of claim 1 further comprising a carbon dioxide source for regulating a level of carbon dioxide in an environment surrounding the well array.

14. The apparatus of claim 1 further comprising a temperature-controlled fluid bath for the well array.

15. The apparatus of claim 14 further comprising a heater for controlling the temperature of the fluid bath.

16. The apparatus of claim 14, wherein the fluid bath is maintained at a temperature of approximately 37° C.

17. The apparatus of claim 1 wherein the wells are arranged on a standard microtiter plate or cell culture plate.

18. The apparatus of claim 1, wherein the driver is associated with at least two tips.

19. The apparatus of claim 1, wherein a separate driver is associated with each tip.

20. A high-throughput flow apparatus for use with an array of wells, the apparatus comprising:

an array of mechanical tips each corresponding to one of the wells;

an interface for positioning each tip within its corresponding well;

a separate post mechanically coupled with each tip and extending beyond a distal end thereof, each post thereby being adapted to contact a floor of its corresponding well and to maintain a predetermined distance between its tip and the floor of the well, each tip driven independently of its corresponding post; and a driver associated with a tip for driving the tip around its respective separate post to impart a shear stress pattern in its corresponding well.

21. The apparatus of claim 20, wherein the shear stress pattern mimics a physiological hemodynamic waveform present in the circulatory system of an organism.

22. The apparatus of claim 21, wherein the physiological hemodynamic waveform comprises at least one of an atheroprotective waveform, an atheroprone waveform, or a waveform that increases stem cell differentiation.

23. The apparatus of claim 21, wherein the organism is at least one of a human or a mouse.

24. The apparatus of claim 20, wherein the shear stress pattern comprises at least one of a steady shear stress pattern or an oscillatory shear stress pattern.

25. The apparatus of claim 20, wherein the shear stress pattern comprises temporal and spatial variations.

26. The apparatus of claim 20, wherein the shear stress pattern has a magnitude of up to 35 dynes/cm$^2$.

27. The apparatus of claim 20, wherein each tip does not contact a surface of its corresponding well.

28. The apparatus of claim 20, wherein each of the wells comprises a feature interfacing with a complementary feature of the corresponding mechanical tip for maintaining radial alignment between the tip and an interior wall of the well.

29. The apparatus of claim 20, wherein a bottom surface of each tip has a flat center and an overall conical shape.

30. The apparatus of claim 20, wherein the driver comprises a variable-speed precision motor.

31. The apparatus of claim 29, wherein the variable-speed precision motor is a stepper motor.

32. The apparatus of claim 20 further comprising a carbon dioxide source for regulating a level of carbon dioxide in an environment surrounding the well array.

33. The apparatus of claim 20 further comprising a temperature-controlled fluid bath for the well array.

34. The apparatus of claim 33 further comprising a heater for controlling the temperature of the fluid bath.

35. The apparatus of claim 33, wherein the fluid bath is maintained at a temperature of approximately 37° C.

36. The apparatus of claim 20 wherein the wells are arranged on a standard microtiter plate or cell culture plate.

37. The apparatus of claim 20, wherein the driver is associated with at least two tips.

38. The apparatus of claim 20, wherein a separate driver is associated with each tip.

39. A high-throughput flow apparatus for use with an array of wells, the apparatus comprising:

an array of mechanical tips each corresponding to one of the wells;

an interface for positioning each tip within its corresponding well;

a separate sleeve associated with each tip and extending a predetermined distance beyond a distal end thereof, each sleeve thereby being adapted to contact a floor of its corresponding well and to maintain the predetermined distance between its tip and the floor of a testing chamber, wherein the testing chamber is defined by a volume captured within an inner diameter of the sleeve, each tip rotatable within its corresponding sleeve; and a driver associated a tip for driving the tip within its respective separate sleeve to impart a shear stress pattern in its testing chamber.

40. The apparatus of claim 39, wherein the separate sleeve is mechanically coupled to its respective tip.

41. The apparatus of claim 39, wherein a bottom surface of each tip has a flat center and an overall conical shape.

42. The apparatus of claim 39, wherein a separate driver is associated with each tip.

43. A high-throughput flow apparatus for use with an array of wells, the apparatus comprising:
- an array of mechanical tips each corresponding to one of the wells;
- an interface for positioning each tip within its corresponding well;
- a separate post associated with each tip and extending a predetermined distance beyond a distal end thereof, each post thereby being adapted to contact a floor of its corresponding well and to maintain the predetermined distance between its tip and the floor of the well, each tip driven independently of its corresponding post; and
- a driver associated a tip for driving the tip around its respective separate post to impart a shear stress pattern in its corresponding well.

44. The apparatus of claim 43, wherein the separate post is mechanically coupled to its respective tip.

45. The apparatus of claim 43, wherein a bottom surface of each tip has a flat center and an overall conical shape.

46. The apparatus of claim 43, wherein a separate driver is associated with each tip.

\* \* \* \* \*